(12) United States Patent
Peterson

(10) Patent No.: US 7,033,379 B2
(45) Date of Patent: Apr. 25, 2006

(54) SUTURE LOCK HAVING NON-THROUGH BORE CAPTURE ZONE

(75) Inventor: James Peterson, Edina, MN (US)

(73) Assignee: Incisive Surgical, Inc., Minnetonka, MN (US)

( * ) Notice: Subject to any disclaimer, the term of this patent is extended or adjusted under 35 U.S.C. 154(b) by 422 days.

(21) Appl. No.: 10/166,161

(22) Filed: Jun. 10, 2002

(65) Prior Publication Data

US 2003/0009196 A1 Jan. 9, 2003

Related U.S. Application Data

(60) Provisional application No. 60/296,796, filed on Jun. 8, 2001.

(51) Int. Cl.
*A61B 17/04* (2006.01)

(52) U.S. Cl. ............................. 606/232; 606/143

(58) Field of Classification Search ............... 606/143, 606/232
See application file for complete search history.

(56) References Cited

U.S. PATENT DOCUMENTS

| | | | |
|---|---|---|---|
| 3,857,396 A | 12/1974 | Williams | |
| 3,874,042 A * | 4/1975 | Eddleman et al. ............ | 251/3 |
| 4,291,698 A | 9/1981 | Fuchs et al. | |
| 5,078,731 A | 1/1992 | Hayhurst | |
| 5,160,339 A | 11/1992 | Chen et al. | |
| 5,171,247 A * | 12/1992 | Hughett et al. ............ | 606/142 |
| 5,234,449 A | 8/1993 | Bruker et al. | |
| 5,258,015 A | 11/1993 | Li et al. | |
| 5,282,832 A | 2/1994 | Toso et al. | |
| 5,330,442 A | 7/1994 | Green et al. | |
| 5,376,101 A | 12/1994 | Green et al. | |
| 5,383,905 A | 1/1995 | Golds et al. | |
| 5,409,499 A | 4/1995 | Yi | |
| 5,413,585 A | 5/1995 | Pagedas | |
| 5,474,572 A | 12/1995 | Hayhurst | |
| 5,476,465 A | 12/1995 | Preissman | |
| 5,514,159 A | 5/1996 | Matula et al. | |
| 5,531,763 A | 7/1996 | Mastri et al. | |
| 5,549,619 A | 8/1996 | Peters et al. | |
| 5,630,824 A | 5/1997 | Hart | |
| 5,645,553 A | 7/1997 | Kolesa et al. | |
| 5,665,109 A | 9/1997 | Yoon | |
| 5,693,060 A | 12/1997 | Martin | |
| 5,735,877 A | 4/1998 | Pagedas | |
| 5,741,281 A | 4/1998 | Martin | |
| 5,776,150 A | 7/1998 | Nolan et al. | |
| 5,810,853 A | 9/1998 | Yoon | |
| 5,951,590 A | 9/1999 | Goldfarb | |

(Continued)

OTHER PUBLICATIONS

Website Print-out: Mitek Products, A Division of ETHICON, Inc., 7 pgs., Copyright 1998-2000.

(Continued)

*Primary Examiner*—Gary Jackson
(74) *Attorney, Agent, or Firm*—Patterson, Thuente, Skaar & Christensen, P.A.

(57) ABSTRACT

A suture lock utilizes a first engaging element and a second engaging element to define a non-through bore capture zone. Each of the engaging elements possesses a surface including at least one mating element that corresponds to a mating element on a surface of the opposing engaging element. When engaged across suture segments, the mating elements apply a frictional holding force to the suture segments. The frictional holding force secures the suture along the length of the suture in the capture zone between the mating elements.

9 Claims, 13 Drawing Sheets

U.S. PATENT DOCUMENTS

| | | |
|---|---|---|
| 5,984,933 A | 11/1999 | Yoon |
| 6,066,160 A | 5/2000 | Colvin et al. |
| 6,074,409 A | 6/2000 | Goldfarb |
| 6,086,608 A | 7/2000 | Ek et al. |
| 6,099,553 A | 8/2000 | Hart et al. |
| 6,106,545 A | 8/2000 | Egan |
| 6,126,677 A | 10/2000 | Ganaja et al. |
| 6,152,934 A | 11/2000 | Harper et al. |
| 6,200,329 B1 | 3/2001 | Fung et al. |
| 6,293,961 B1 | 9/2001 | Schwartz et al. |
| 6,358,271 B1 | 3/2002 | Egan et al. |
| 6,409,743 B1 | 6/2002 | Fenton, Jr. |

OTHER PUBLICATIONS

Clinical Paper: *Laceration—Repair,* 8 pgs., Aug. 2000.

Website Print-out: *Comparison of Tensile Properties of the Hand-Knotted Braided Suture and AxyaLoop™ Ultrasonically Welded Suture,* M. Apreleva, B. Swanson, J.C. Richmond, Axya Medical, Inc., Beverly, MA, 5 pgs., Nov.-Dec. 2000.

\* cited by examiner

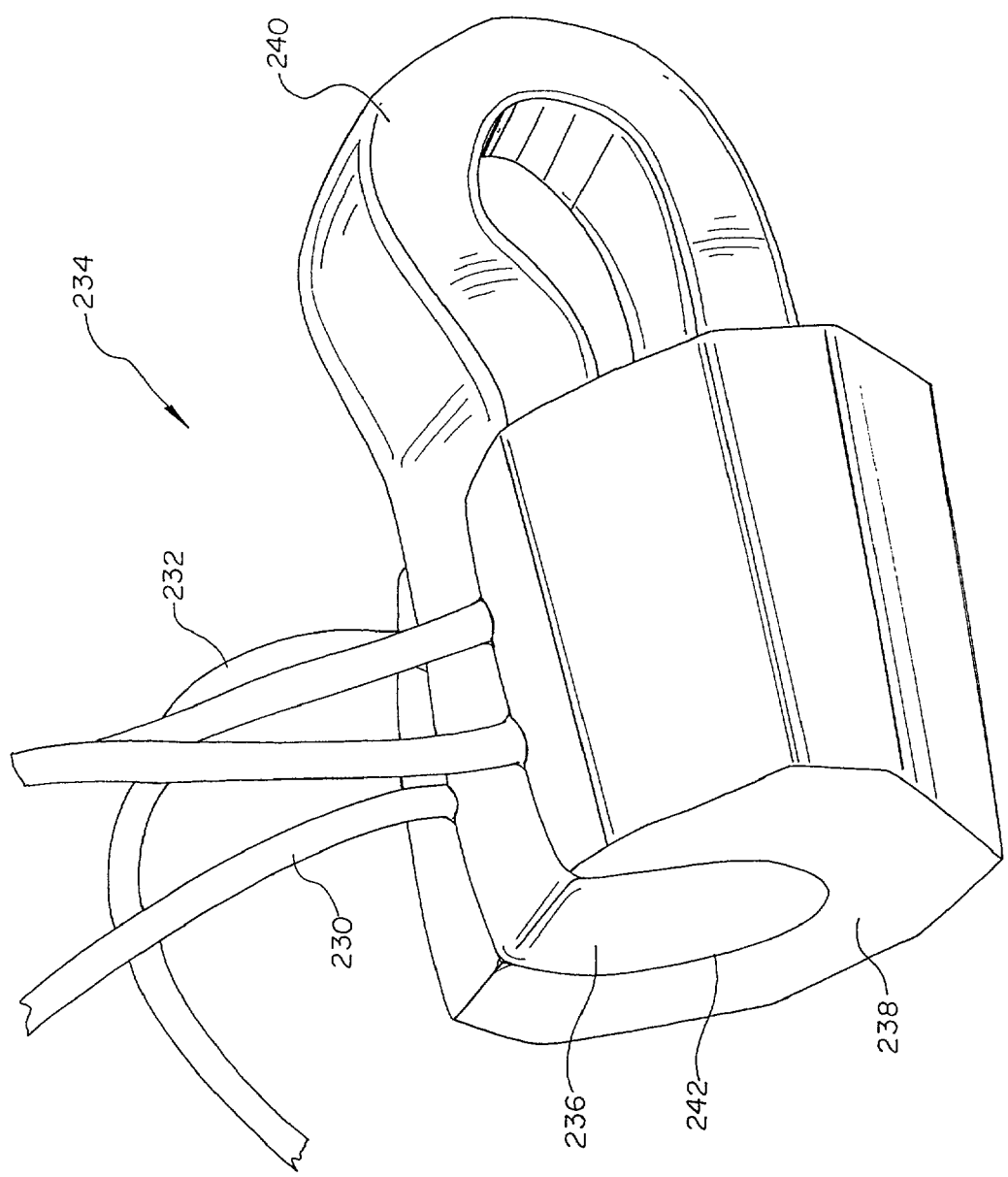

SUTURE LOCK HAVING NON-THROUGH BORE CAPTURE ZONE

CLAIM TO PRIORITY

This application claims benefit of U.S. Provisional Application No. 60/296,796 filed Jun. 8, 2001, entitled, "SUTURE CLIP," which is incorporated herein by reference.

FIELD OF THE INVENTION

The present invention relates generally to a tissue closure apparatus and methods. More particularly, the present invention relates to a suture lock having first and second engaging elements that create a non-through bore capture zone that frictionally secures a suture when the engaging elements are mated.

BACKGROUND OF THE INVENTION

When an opening in tissue is created either through an intentional incision or an accidental wound or laceration, biological healing of the opening commences through the proximity of living tissue. If the opening is very large or if its location subjects the wound to continual movement, a physician will seek to forcibly hold the sides of the incision or wound in close proximity so as to promote the healing process. The most prevalent method for forcibly holding tissue closed is through the use of a suture or "stitches." Sutures also are used to ligate (tie-off) vessels, arteries and fluid carrying ducts by encircling the vessels and occluding flow within the vessel by tightening the suture around the vessel. Sutures may also be placed to suspend or stabilize anatomic structures or to secure or locate implants.

Since at least the second century, practitioners have used sutures in various forms. The early Greeks used sutures comprised of gut. As time passed other natural materials including leather, horsehair, flax, cotton and silk were also used. Over the past century, advances in the material sciences have fostered the creation of polymeric sutures and specially formulated synthetic sutures that are readily absorbed by the body.

Despite the changes and advances in physical composition, the basic suture method has remained unchanged. In order to suture a tissue incision or wound two items are required. The first item is a tissue-piercing device, typically a needle that includes a holding mechanism. The second item is a length of suture that will interface with this holding mechanism. The physician forcibly approximates two sides of the incision or wound being sure that the living tissue is brought into contact. The physician then inserts the tissue piercing device through one side of the tissue and into and through the second side. As the tissue piercing device passes through the tissue, it pulls the suture material through as well so that the suture spans the tissue incision or wound. Using the suture, the physician then ties a knot and cinches the incision or wound closed. Depending on the size of the opening, a physician will repeat the process to effectuate closure across the length of an incision or wound.

Due to advances in modern surgical procedure, sutures are being used in many locations throughout the body including internal sites accessed by endoscopic, laparoscopic, or orthoscopic tools. Depending on the location, access to the surgical site may be limited creating difficulties with proper knot tying. These difficulties can lead to ineffective suture closure as well as increased closure times. Ultimately, these difficulties lead to increased surgical risks to the patient as well as adverse economic effects derived from longer closure times.

Recognizing the inherent difficulties associated with suture knots, a number of different approaches have been pursued by inventors. One approach has been to develop tools or apparatus for tying or assisting in tying the suture. Examples of such inventions include U.S. Pat. No. 5,776,150 to Nolan et al., U.S. Pat. No. 5,984,933 to Yoon, and U.S. Pat. No. 6,152,934 to Harper et al.

An altogether different approach for endoscopic or open surgery applications has been to replace the suture knot completely. Typically, this is accomplished by providing a mechanical gripping device that holds the ends of the suture in place. In some instances, this gripping device has taken the form of a one-piece clip. Examples of one-piece clips include U.S. Pat. No. 5,160,339 to Chen et al., U.S. Pat. No. 5,234,449 to Bruker et al., U.S. Pat. No. 5,330,442 to Green et al., U.S. Pat. No. 5,409,499 to Yi, U.S. Pat. No. 5,645,553 to Kolsea et al., and U.S. Pat. No. 5,665,109 to Yoon. In other cases, the device has taken the form of a two-piece clip. An example of a two-piece clip includes U.S. Pat. No. 5,282,832 to Toso et al. In other instances, the device requires a bore for fenestration or threading of the suture through the bore so the suture can be held by a knot or an interference fit. Examples of devices which use a bore include U.S. Pat. No. 5,514,159 to Matula et al., U.S. Pat. No. 5,630,824 to Hart, U.S. Pat. No. 6,066,160 to Colvin et al., U.S. Pat. No. 6,126,677 to Ganaja et al., U.S. Pat. No. 6,200,329 to Fung et al., and U.S. Pat. No. 6,293,961 to Schwartz et al. Finally, other approaches have used gripping devices created through welding of suture material or other holding elements. Examples include U.S. Pat. No. 6,358,271 to Egan et al., and U.S. Pat. No. 6,106,545 to Egan.

While these mechanical gripping devices have improved the speed and reliability of internal sutures, there remain considerable drawbacks. Many of the aforementioned gripping devices require fenestration of the suture through a bore prior to the closure of the device. Depending on the suture location, threading through this fenestration may be nearly as difficult and time consuming as tying a knot. Many of the devices have closure mechanisms that make it nearly impossible to design applicators capable of reloading and applying additional fasteners without withdrawing the applicator from the suture site. In addition, many of the applicators have little or no adjustment capacity once the closure device is applied should a physician need to further cinch and/or adjust the suture tension. What is needed in the art is a suture clip design that overcomes these limitations.

SUMMARY OF THE INVENTION

The suture lock of the present invention uses a first engaging element and a second engaging element to define a non-through bore capture zone. Each of the engaging elements possesses a surface including at least one mating element that corresponds to a mating element on a surface of the opposing engaging element. When engaged across suture segments, the mating elements apply a frictional holding force to the suture segments. The frictional holding force secures the suture along the length of the suture in the capture zone between the mating elements.

The suture lock of the present invention overcomes the limitations of the prior art. The locking mechanism of the suture lock provides enough strength so that fenestration of the suture through a suture lock bore is not required. In addition, the suture lock is designed for use with an applicator that allows the placement of multiple fasteners without withdrawing and reloading the applicator. Finally, the suture lock can be readily adjusted, either through disengagement of the mating elements or through application of a frictionally directing surface on the mating element, which provides the physician ample opportunity to cinch, tighten, or otherwise adjust the tension of the suture lock.

BRIEF DESCRIPTION OF THE DRAWINGS

FIG. 15 is a perspective view of an alternative embodiment of the suture lock.

DETAILED DESCRIPTION OF THE PREFERRED EMBODIMENTS

Figure 1:
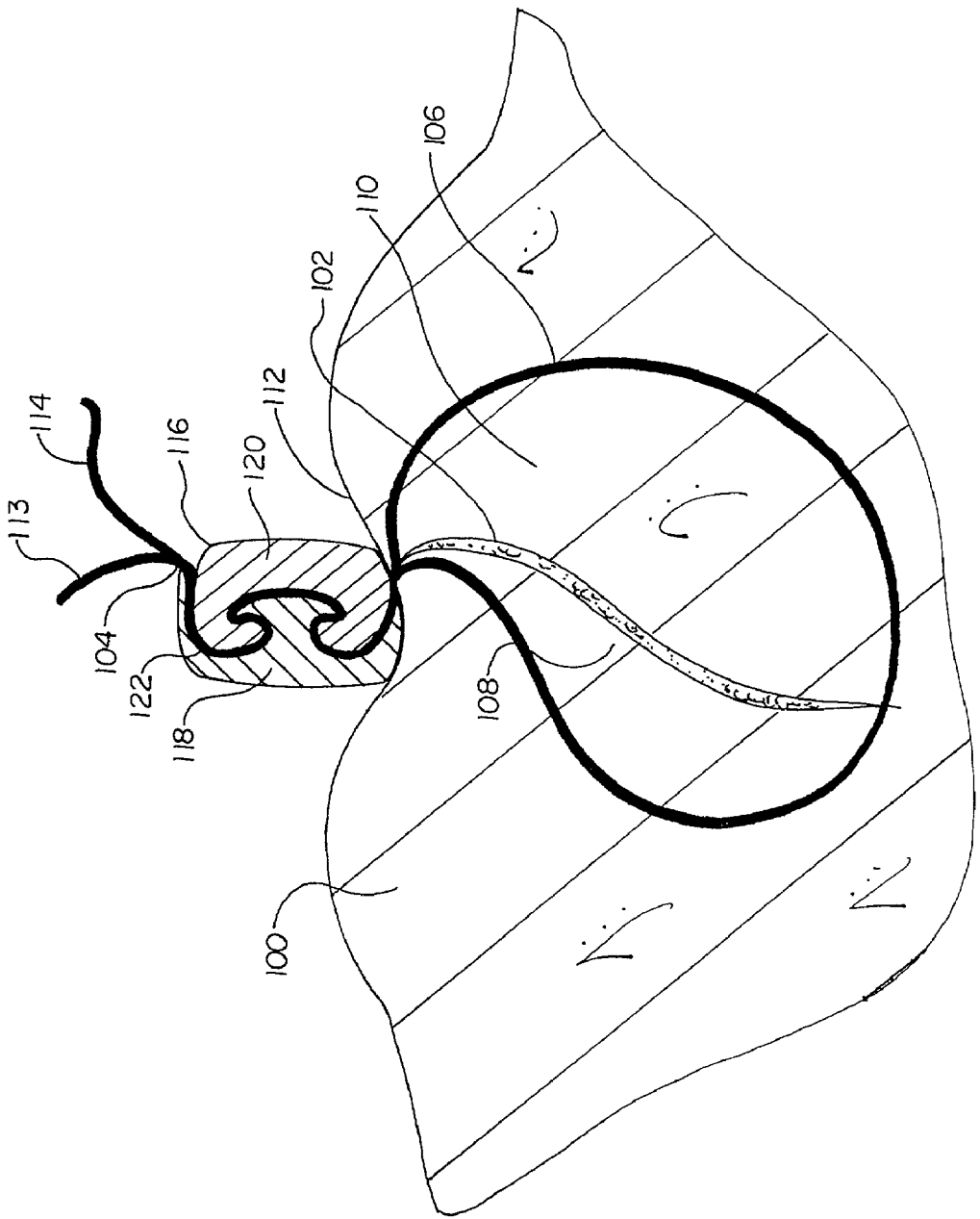
FIG. 1 is a sectional view of a completed suture lock installation.

FIG. 1 depicts a tissue closure using the suture lock of the present invention. Tissue 100 is separated by a tissue opening or incision 102. Using a length of suture 104, a physician draws together living tissue 100 through the use of a suture loop 106. Suture loop 106 forcibly draws opposing layers 108 and 110 of living tissue 100 into intimate physical contact. Suture 104 exits the tissue 100 at a tissue surface 112. Where suture 104 exits the tissue surface 112, a pair of suture ends or segments 113 and 114 are present. Suture 104 is held in place at the tissue surface 112 through the use of a suture lock 116, as will be described.

For purposes of the present invention, it will be understood that suture lock 116 can be used to secure suture segments 113 and 114 in a variety of configurations. While suture 104 is typically used to close an opening, wound, or incision 102, it will be recognized that suture lock 116 may be used with sutures 104 for other purposes, such as to ligate (tie-off) vessels, arteries, and fluid carrying ducts, to suspend or stabilize anatomic structures, or to secure or ligate implants. While it is typical for a suture loop 106 to have a pair of suture segments 113 and 114 in the form of loose ends, it will also be recognized that suture segments 113 and 114 could be located proximal to an end of suture 104, that multiple suture locks 116 could be used along a section of suture 104, that more than two suture segments may be secured and that suture segments 113 and 114 may belong to different pieces of suture 104, or even that a single suture segment 113 may be secured in those instance where suture lock 116 is to be used as a chock to prevent suture loop 106 from advancing through a passage or where a separate suture lock 116 is used for each suture segment 113, 114. It is also recognized that a suture lock 116 could come preattached to a length of suture 104 for use in tissue ligation. A length of suture 104 would be deployed with each suture lock 116. One end of suture 104 would be attached to suture lock 116 and the other end would be free to be placed around the tissue to be ligated. The free end could then be placed within the suture lock 116 and secured to rapidly and effectively achieve ligation.

Suture lock 116 is comprised of a first engaging element 118 and a second engaging element 120. Suture segments 113 and 114 are brought into proximity so that first engaging element 118 and second engaging element 120 can be placed on opposing sides of suture segments 113 and 114 such that suture segments 113 and 114 are effectively positioned within a non-through bore capture zone 122. First engaging element 118 and second engaging element 120 are physically coupled. The physical coupling of first engaging element 118 and second engaging element 120 serves to capture suture segments 113 and 114 without further manipulation of suture 104. The interconnection of at least a portion of first engaging element 118 and with at least a portion of second engaging element 120 creates a non-through bore capture zone 122 for suture segments 113 and 114. When engaging elements 118 and 120 are mated, capture zone 122 places tension on suture segments 113, 114 through friction between first engaging element 118 and second engaging element 120. This friction results in suture loop 106 being held tight at the position along suture 104 of suture lock 116 such that opposing layers 108 and 110 of tissue 100 remains in physical contact.

Preferably, capture zone 122 is defined in the form of a tortuous path created by the interface of engaging elements 118 and 120 with suture segments 113, 114. As will be described, preferably suture segments 113, 114 are placed in capture zone 122 generally perpendicular to a longitudinal axis of the suture lock 116. It will be recognized, however, that numerous configurations of engaging elements 118 and 120 can be created to define a variety of combinations that produce a capture zone 122 which may include suture segments 113, 114 being oriented diagonally with respect to a longitudinal axis of the suture lock 116, suture segments 113, 114 lapping back on each other or over each other, suture segments 113, 114 entering and exiting only one edge of engaging elements 118 and 120, or suture segments entering and exiting different edges of engaging elements 118 and 120. It will also be understood that capture zone 122 encompasses a three dimensional space when engaging elements 118 and 120 are not mated, and a two-dimensional plane when the mated portions of engaging elements 118 and 120 are mated, with the preferred tortuous path being defined in this plane as a pair of single-dimensional lines where the suture segments 113, 114 are retained within the mated engaging elements 118 and 120. The critical feature of capture zone 122 is that no through bore is defined through which suture 104 must be fenestrated. Instead, suture segments 113, 114 can simply be placed into or laid along the capture zone 122 without the need for any threading of suture 104 through a bore or fenestration.

Figure 2:
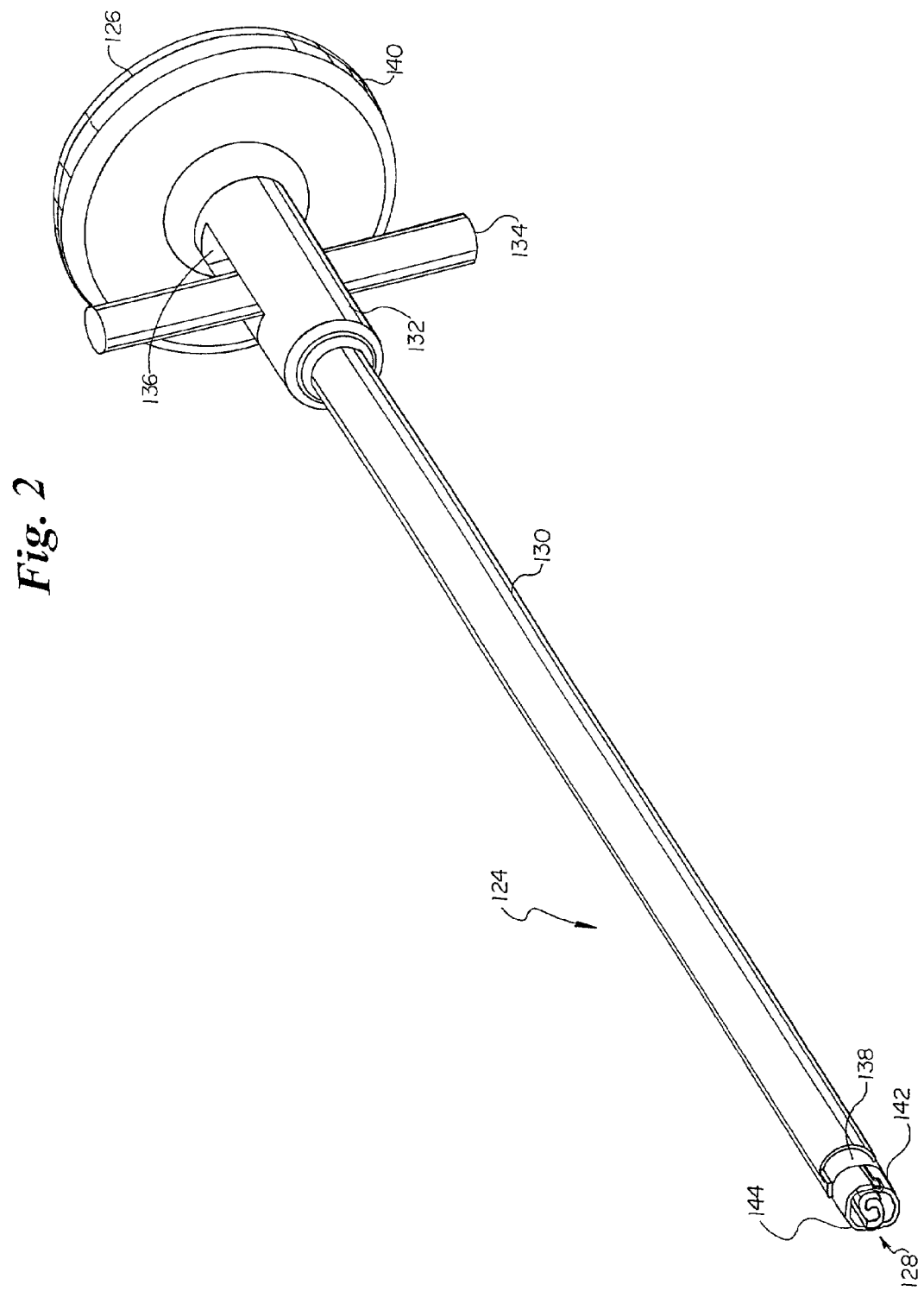
FIG. 2 is a perspective view of the suture lock apparatus with the applicator in a closed configuration.
Figure 3:
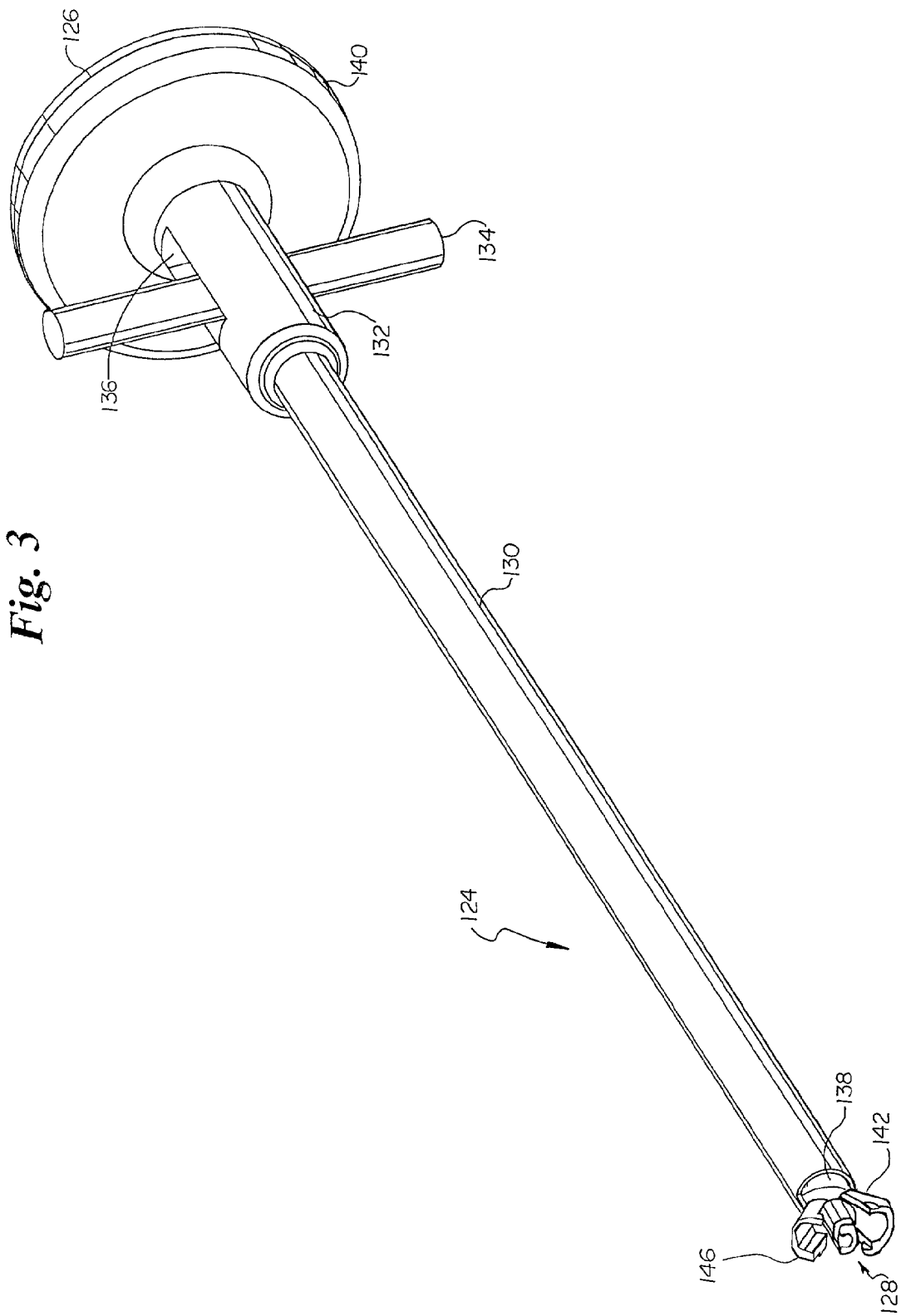
FIG. 3 is a perspective view of the loaded suture lock apparatus with the applicator in an open configuration.

FIG. 2 contains a view of a preferred embodiment of suture lock applicator 124. The applicator 124 comprises a proximal end 126 and a distal end 128. The applicator 124 includes an insertion tube 130, an actuator tube 132 and an actuator handle 134. Actuator handle 134 is mounted in an actuator channel 136. Insertion tube 130 and actuator tube 132 define an applicator bore 138 that is continuous from the distal end 128 to an operator grip 140. Located at distal end 128 of applicator 124 is a clip interface 142 for manipulating suture lock 116. Clip interface 142 is shown in a partially open configuration 144. FIG. 3 shows another view of the applicator 124 in which clip interface 142 is shown in a completely open configuration 146.

Figure 4:
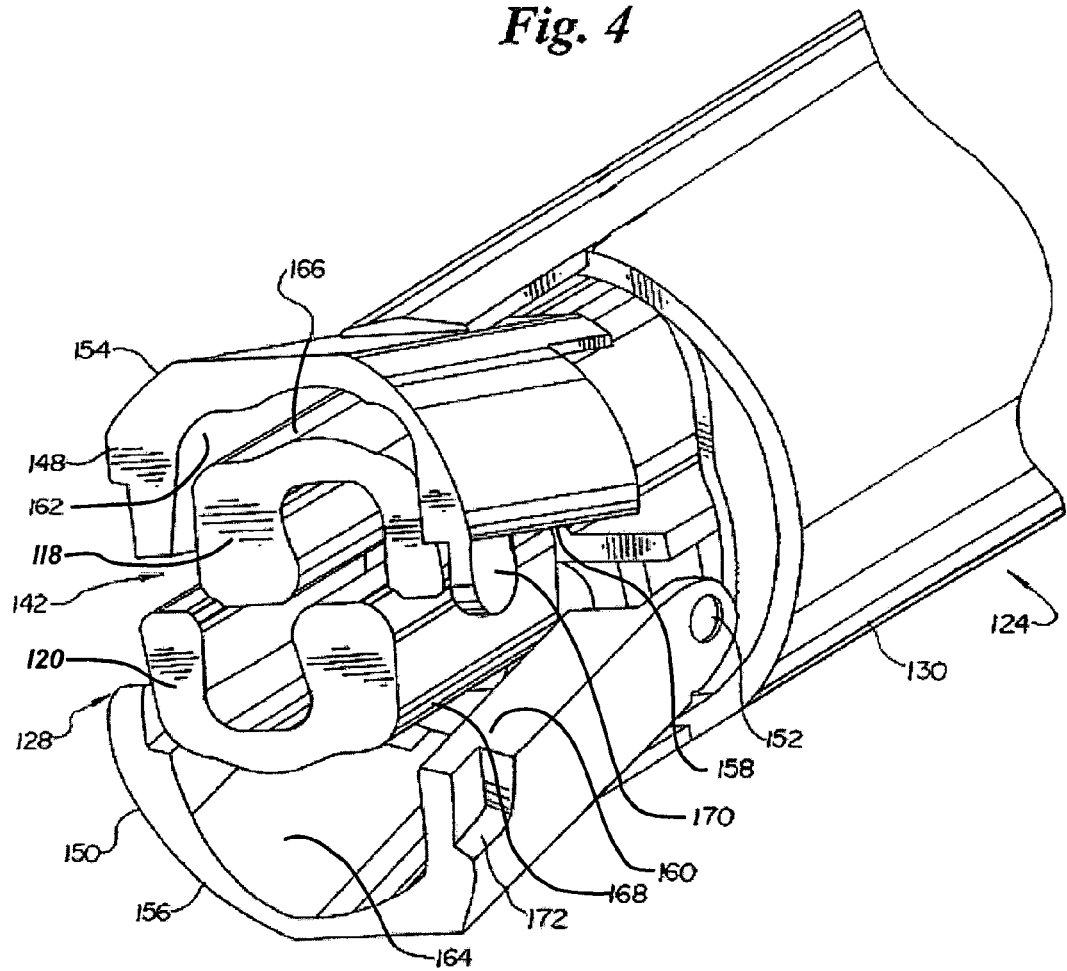
FIG. 4 is a perspective view of the applicator head in an open configuration.

FIG. 4 provides an enlarged view of a preferred embodiment of the distal end 128 of applicator 124. Clip interface 142 is comprised of a first insertion member 148 and a second insertion member 150. First insertion member 148 and second insertion member 150 are physically coupled by a hinge 152. Both first insertion member 148 and second insertion member 150 preferably include an arcuate exterior surface 154, 156, an interface surface 158, 160, and an interior concave surface 162, 164. The interior concave surfaces 162, 164 correspond to an exterior surface 166, 168 on first engaging element 118 and second engaging element 120. First insertion member 148 also includes an insertion tab 170 projecting from the interface surface 158. Second insertion member 150 includes an insertion channel 172 designed to interface with insertion tab 170.

It is to be understood that the preferred embodiment of applicator 124 has been described for illustrative purposes only and could have a wide range of alternative configurations without departing from the spirit or scope of the disclosed invention. Alternatives could include individual lock applicators, manually loadable applicators, or applicators providing locking feedback to a user. Applicators may be specifically configured to apply suture locks in different applications, such as endoscopic or orthoscopic surgery, or applicators may have features adapted for particular body parts, such as a applicators having larger or smaller distal ends 128 with or without stabilizer or guide structures. Additionally, applicator 124 along with suture locks 116 may be configured in various sizes depending upon the application and the dimensions of the suture material 104 being utilized.

Figure 5:
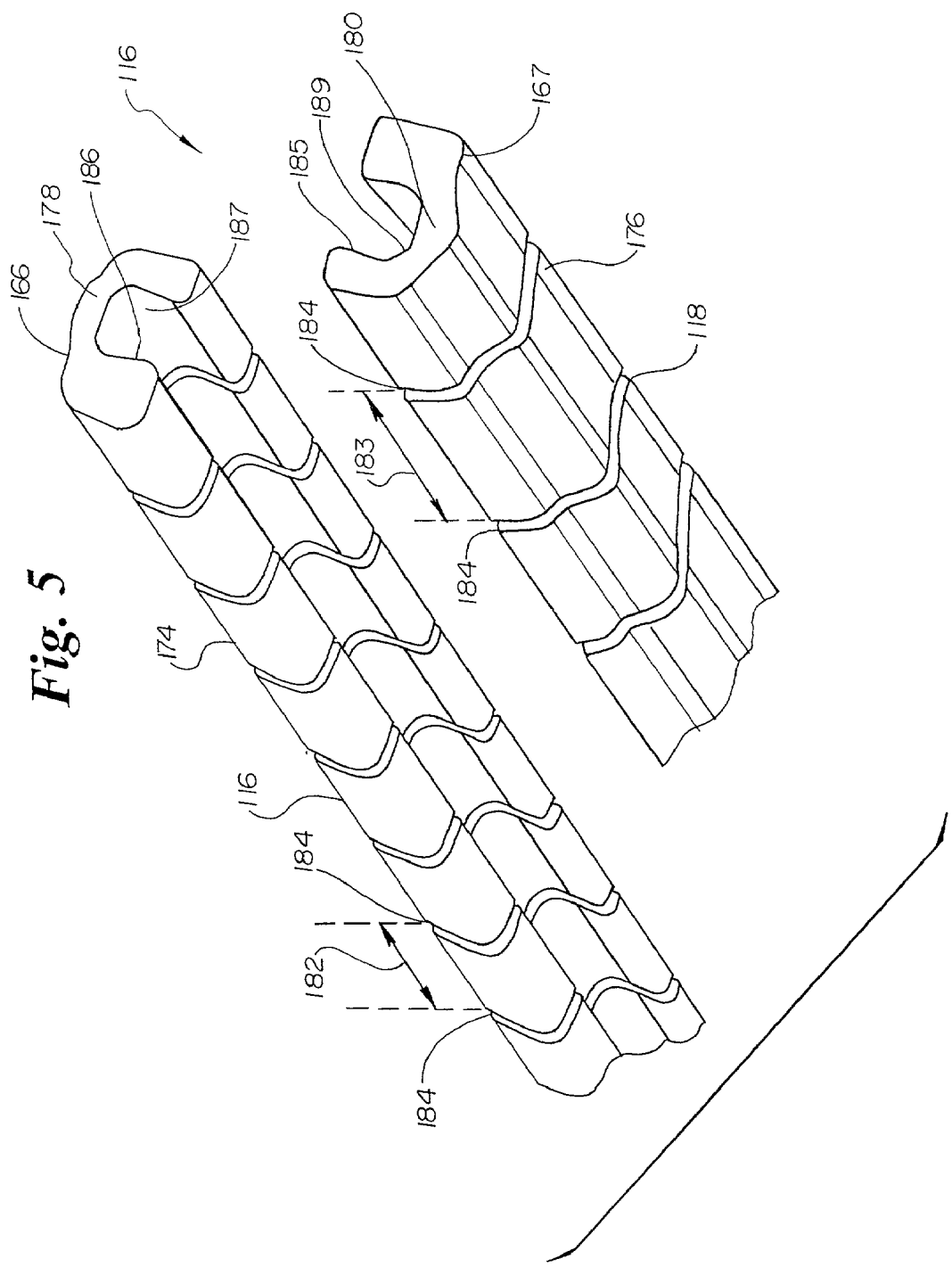
FIG. 5 is a perspective view of the suture lock designed for multiple applications at an application site.

FIG. 5 depicts the preferred embodiment of a continuous series of first engaging elements 118 and second engaging elements 120. In the preferred embodiment of applicator 124, a plurality of first engaging element 118 reside on a first clip 174 and a plurality of second engaging element 120 reside on a second clip 176. First engaging element 118 possesses a first cross-section 178. Second engaging element possesses a second cross-section 180. In the preferred embodiment, first cross-section 178 and second cross-section 180 are identical providing a high-degree of repeatability and efficiency in the manufacturing process. First engaging element 118 has a first longitudinal element length 182. Second engaging element 120 includes a second longitudinal element length 183. In the preferred embodiment, first element length 182 and second element length 183 are equal. Preferably, a continuous piece of material is used to create an interconnected series of the first and second engaging elements 118, 120. First element length 182 and second element length 183 are both defined along these continuous strips of material by a series of scored indents 184.

A first cross-section 178 is defined by a first exterior surface 166 and a first interior surface 186. Second cross-section 180 is defined by a second exterior surface 167 and a second interior surface 185. A first mating portion 187 is defined as that portion of the first exterior surface 166 and first interior surface 186 that are designed to come into physical contact with second engaging element 120. Similarly, a second mating portion 189 is defined as that portion of the second exterior surface 176 and second interior surface 185 that are designed to come into physical contact with first engaging element 118. The interaction of first mating portion 187 and second mating portion 189 creates a locking force. In the preferred embodiment, first mating portion 187 and second mating portion 189 are not identical, even though first cross-section 178 and second cross-section 180 are identical and are not limited to only the interior surfaces 186, 185. It will be easily recognizable from the following disclosed embodiments that the first mating portion 187 and the second mating portion 189 can include a wide range of alternative geometries including, but not limited to, male style projecting elements in combination with female style receiving elements in which the mating portions 187 and 189 may be mirror images of each other and may include only portions of the interior surfaces 186, 185.

Figure 6:
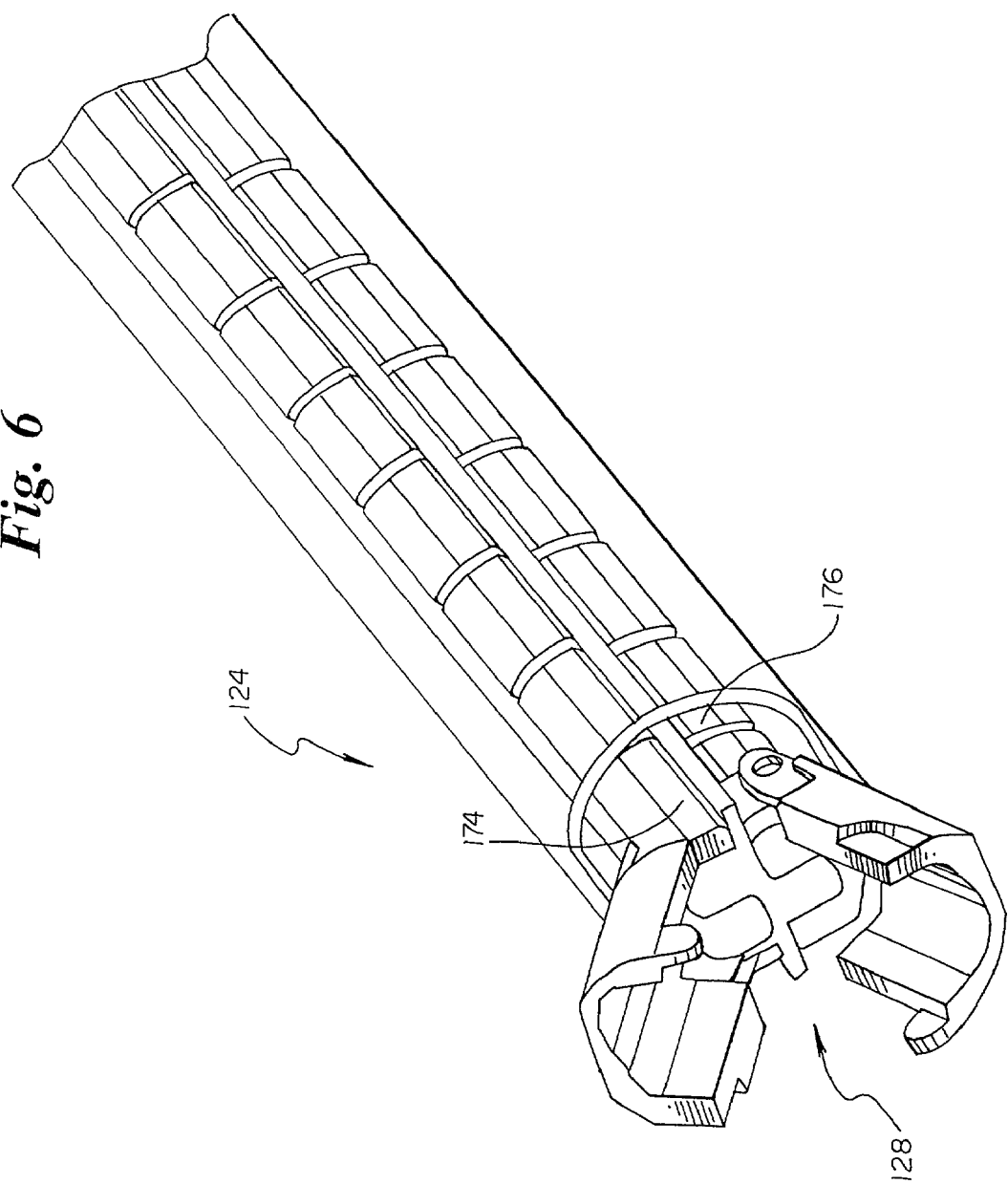
FIG. 6 is a sectional perspective view of the applicator.

In the preferred embodiment, first engaging element 118 and second engagement 120 are made of bioabsorbable materials including but not limited to poly lactic acid and poly lactic-glycolic acid. In special applications, it may be advantageous to fabricate the first engaging element 118 and the second engaging element 120 from nonabsorbable materials including, but not limited to, stainless steel, titanium, cobalt chrome and polyethylene. Alternatively, first engaging element 118 and second engaging element 120 could be made from any combination of absorbable and nonabsorbable biocompatible materials. FIG. 6 depicts a sectional view of the distal end 128 of applicator 124. First clip 174 and second clip 176 reside within applicator bore 128. The presence of first clip 174 and second clip 176 allow the user to deliver multiple suture locks 116 to a suture site. Although suture locks 116 are shown as residing on a center channel of clips 174 and 176, it will be recognized that alternative configurations for retaining and carrying multiple locks 116 can be used, such as providing locks 116 within a channel, on a tape or backing carrier, or in a reservoir with a feed system.

Figure 7:
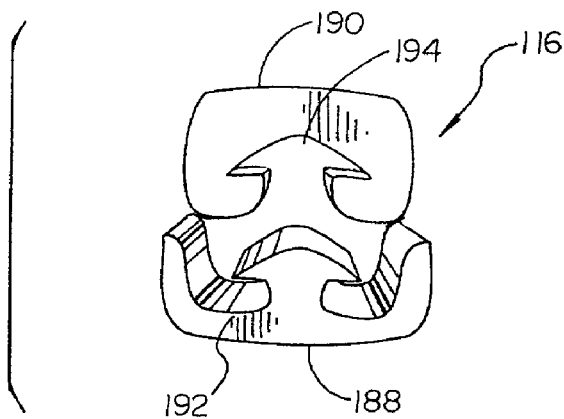
FIG. 7 is an exploded end view of an alternative embodiment of the suture lock.

FIG. 7 depicts an alternative embodiment of suture lock 116. In this embodiment, suture lock 116 is comprised of a male engaging element 188 and female engaging element 190. Male engaging element 188 includes a barbed projection 192. Female engaging element 190 includes a barbed cavity 194. Barbed cavity 194 is designed to for physical coupling with barbed projection 192.

Figure 8:
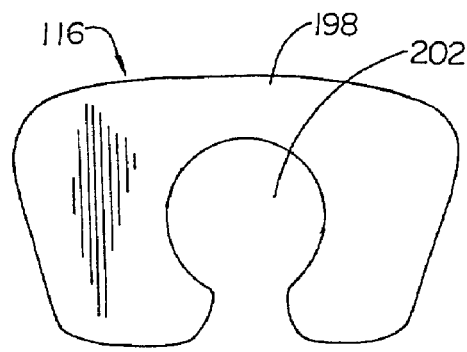
FIG. 8 is an exploded end view of an alternative embodiment of the suture lock.

FIG. 8 depicts another embodiment of suture lock 116. In this embodiment, suture lock 116 is comprised of male engaging element 196 and female engaging element 198. Male engaging element 196 includes a bulbous projection 200. Female engaging element 198 includes a bulbous cavity 202. Bulbous cavity 202 is designed for physical coupling with bulbous projection 200.

Figure 9:
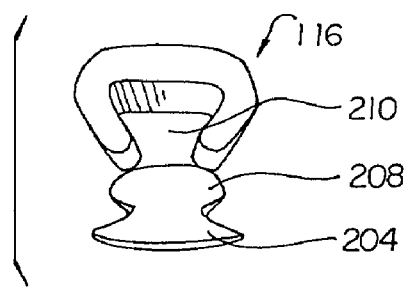
FIG. 9 is an exploded end view of an alternative embodiment of the suture lock.

FIG. 9 depicts another embodiment of suture lock 116. In this embodiment, suture lock 116 comprises male engaging element 204 and female engaging element 206. Male engaging element 204 includes a flanged projection 208. Female engaging element 206 includes a flanged cavity 210. Flanged cavity 210 is designed for physical coupling with flanged projection 208.

Figure 10:
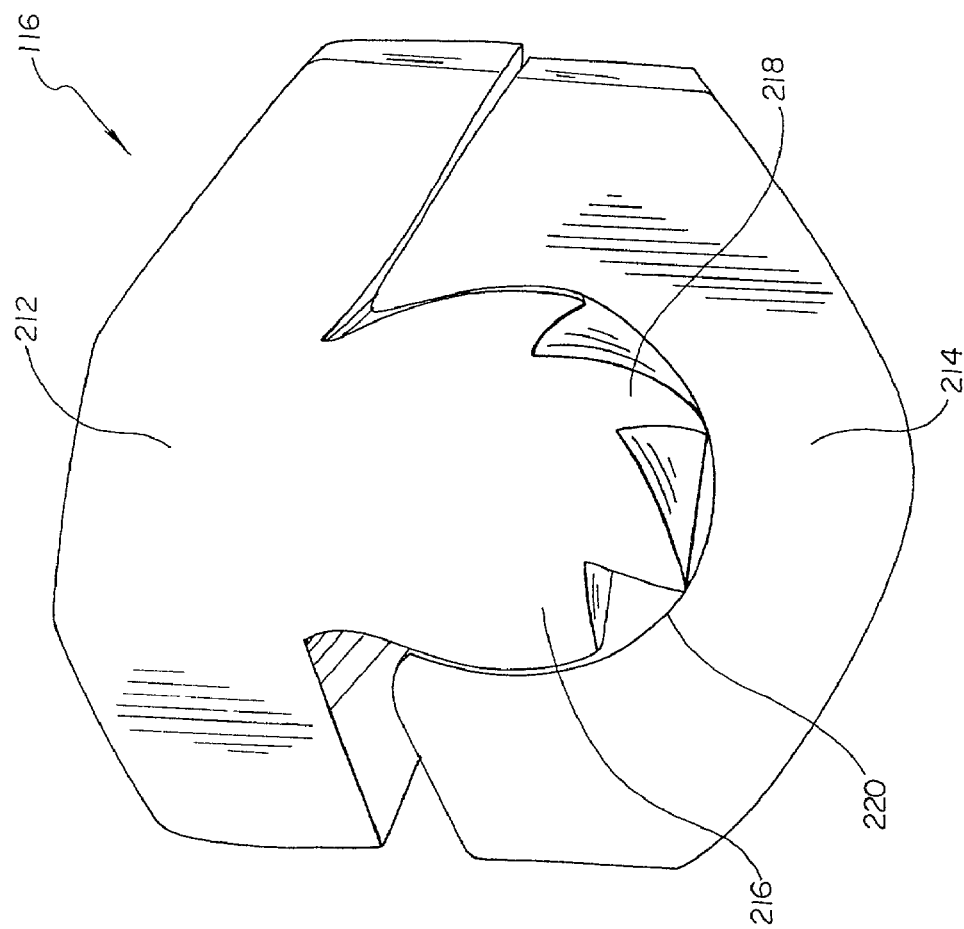
FIG. 10 is an end view of an alternative embodiment of the suture lock.

FIG. 10 depicts another embodiment of suture lock 116. In this embodiment, suture lock 116 comprises male engaging element 212 and female engaging element 214. Male engaging element 212 includes a cylindrical projection 216 including a series of notched projections 218. Female engaging element 214 includes a cylindrical cavity 220. Cylindrical cavity 220 is designed for physical coupling with cylindrical projection 216. In addition to providing for friction holding of suture 104, notched projections 218 provide a directional force such that a physician can cinch suture loop 106 in one direction while restraining suture 104 movement in the other direction.

Figure 11:
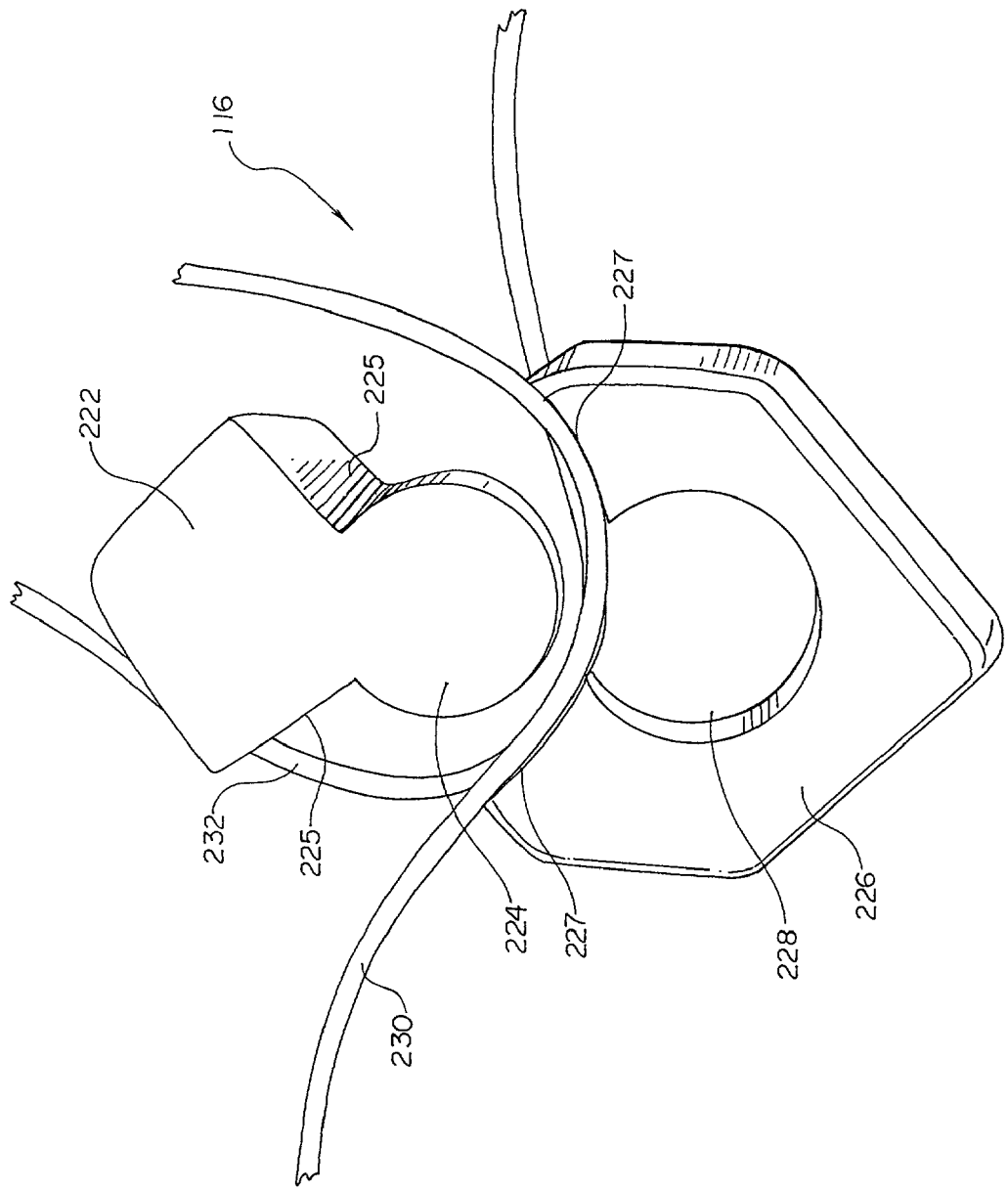
FIG. 11 is an exploded end view of an alternative embodiment of the suture lock.
Figure 12:
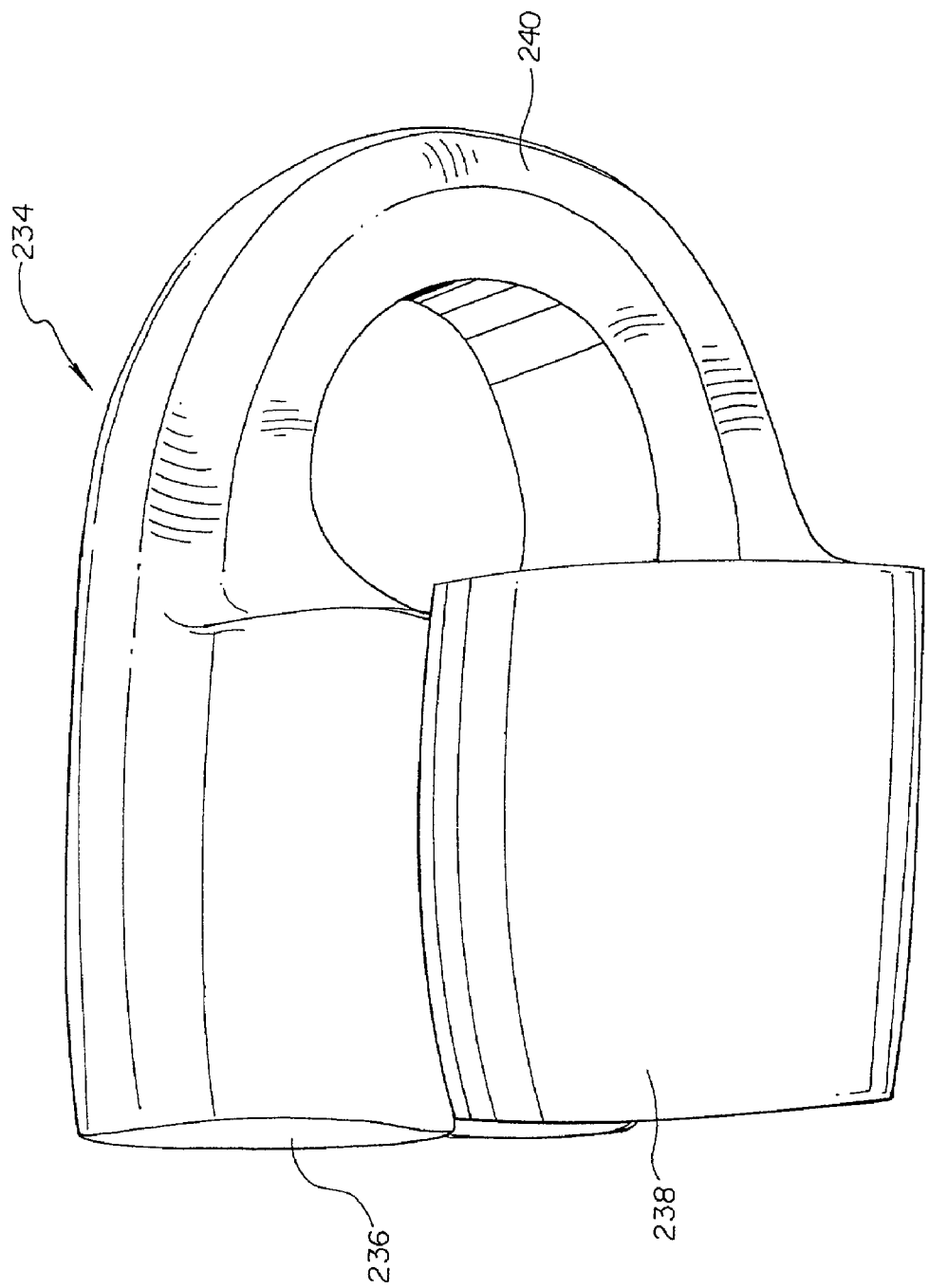
FIG. 12 is a side view of an alternative embodiment of the suture lock.
Figure 13:
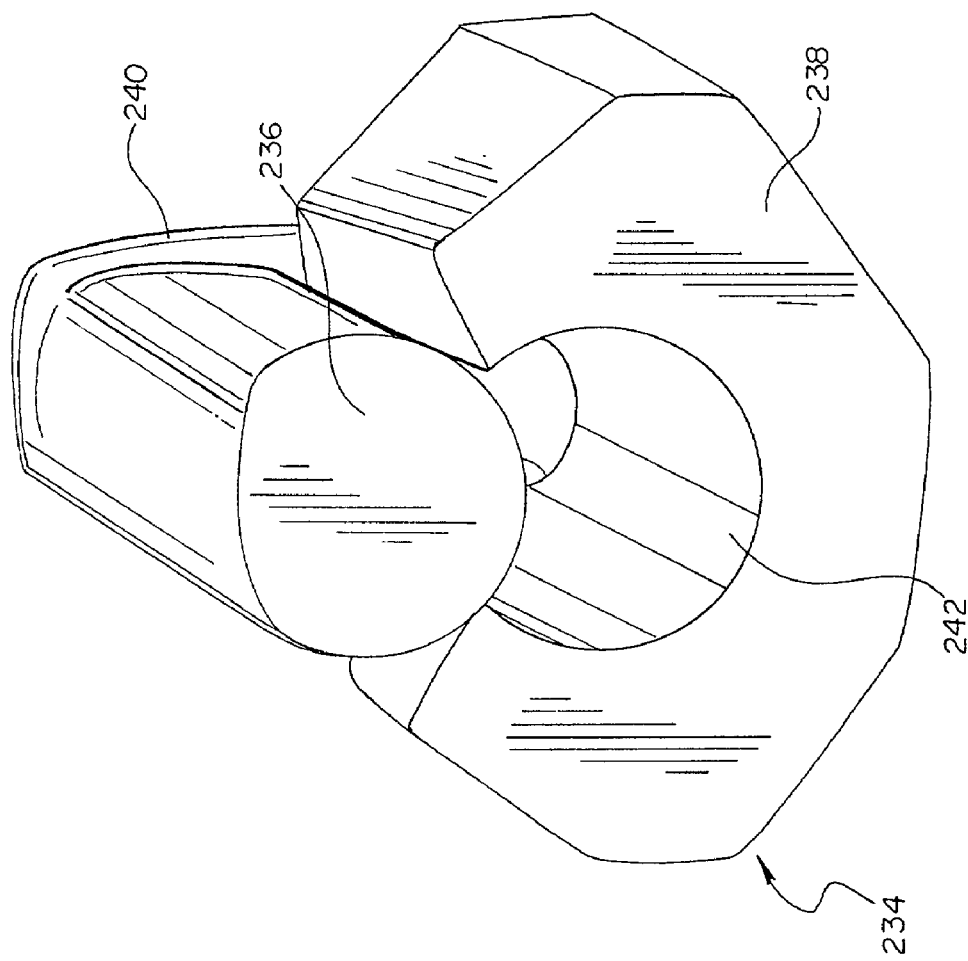
FIG. 13 is an end view of an alternative embodiment of the suture lock.
Figure 14:
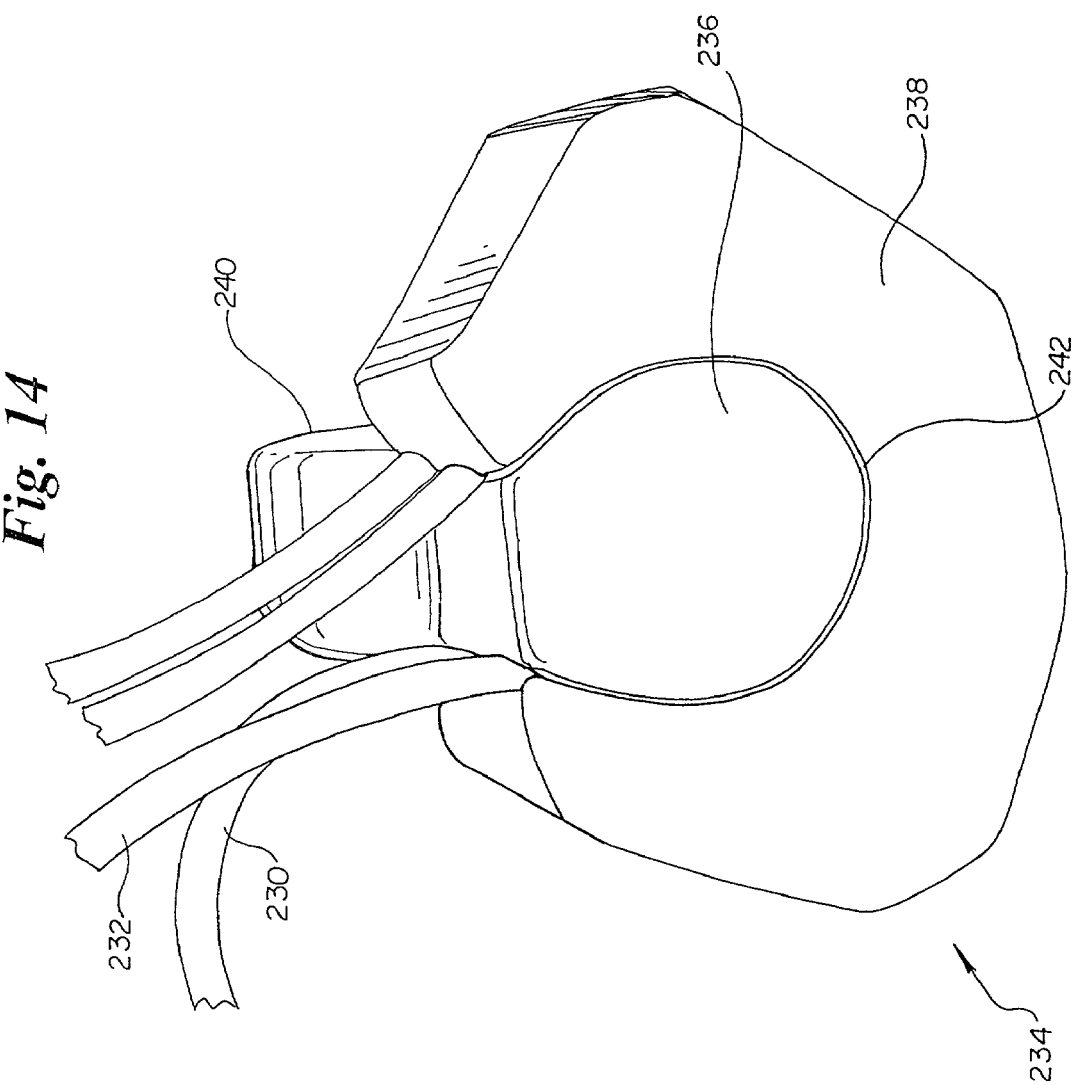
FIG. 14 is an end view of an alternative embodiment of the suture lock.

FIG. 11 depicts another embodiment of suture lock 116. Male engaging element 222 includes a cylindrical projection 224 above which are angled surfaces 225. Female engaging element 226 includes cylindrical cavity 228 above which also are angled surfaces 227. Cylindrical cavity 228 is designed for physical coupling with cylindrical projection 224 with the angled surfaces 225 and 227 serving as both guide and stop structures for the mating of engaging elements 222 and 226. In this embodiment, suture lock 116 is being used to hold both a first suture 230 and a second suture 232.

Preferably, suture lock 116 is comprised of first and second engaging elements 118, 120 that are physically separate from each other to permit application in a continuous series as shown, for example, in FIGS. 2, 3, 4, 5, and 6. FIGS. 12, 13, 14, and 15 depict an alternative one-piece suture lock 234. The one-piece suture lock 234 includes a cylindrical insertion member 236 and a receiver member 238 at opposing ends of a hinge member 240. Receiver member 238 contains a cylindrical receiver bore 242. Cylindrical receiver bore 242 has a cross-section designed for physical coupling with cylindrical insertion member 236. In this embodiment, suture lock 116 is being used to hold both first suture 230 and second suture 232. The design of one-piece suture lock 234 may be better suited for manual use of the present invention with the hinge member 240 allowing for one handed manual application and operation by a surgeon without the need for an applicator.

In practice, the preferred embodiment of the suture lock 116 is applied by a physician during the closing of a tissue incision or opening 102. The physician draws together tissue 100 with suture loop 106. Being sure that living tissue 100 from both sides of tissue incision 102 are in intimate contact, the physician directs distal end 128 of suture lock applicator 124 such that clip interface 142 encompasses suture 104 between first engaging element 118 and second engaging element 120. Using actuator handle 134, the physician biases suture lock applicator 124 such that clip interface 142 moves from an open configuration to a closed configuration. As clip interface 142 moves into the closed configuration, first engaging element 118 and second engaging element 120 are physically coupled due to the compatibility of cross-section 178. More specifically, the forced approximation of first mating portion 187 and second mating portion 189 creates an interference fit resulting in the physical connection of first engaging element 118 and second engaging element 120. The interconnection of first engaging element 118 and second engaging element 120 serves to capture suture 104 in a tortuous path of capture zone 122 along first mating portion 187 and second mating portion 189. As clip interface 142 closes, the first engaging element 118 is snapped off of first clip 174 at scored indent 184 by the first insertion member 148 and the second insertion member 150. At the same time, the same process snaps off second engaging element 120 from second clip 176. The tortuous path of capture zone 122 supplies a frictional holding force to suture loop 106 thus eliminating the need for a suture knot. The physician then has the option of withdrawing the suture lock applicator 124 or advancing the first clip 174 and second clip 176 with the actuator handle 134 for the purpose of capturing additional suture 104 at the same tissue incision 102.

Although the present invention has been described with reference to preferred embodiments, workers skilled in the art will recognize that changes may be made in form and detail without departing from the spirit or scope of the present invention.

What is claimed:

1. A suture lock for securing a first segment and a second segment of a suture, the suture lock comprising:
    a first engaging element and a second engaging element, each engaging element having a surface including at least a mating portion which is opposed to and configured to mate with a corresponding mating portion of a surface of the other engaging element, the mating portions defining a non-through bore capture zone when not mated into which a user locates the first segment and the second segment of the suture such that the first segment and the second segment of the suture are frictionally secured along at least a portion of the capture zone when the mating portions are mated wherein at least one of the mating portions includes at least one surface providing a frictional direction such that the first and second suture segments are restrained from movement in one longitudinal direction of the suture segments and a permitted movement in the other longitudinal direction.

2. The suture lock of claim 1, wherein cross-sections of the mating portions of the first engaging element and the second engaging element are identical.

3. The suture lock of claim 1, wherein the mating portions comprise a male element and a female element.

4. The suture lock of claim 1, wherein the engaging elements are made of a bioabsorbable material.

5. The suture lock of claim 1, wherein the engaging elements are made at least in part of a non-absorbable biocompatible material.

6. A suture lock for securing a first segment and a second segment of a suture, the suture lock comprising:
    a first engaging element and a second engaging element, each engaging element having a surface including at least a mating portion which is opposed to and configured to mate with a corresponding mating portion of a surface of the other engaging element the mating portions defining a non-through bore capture zone when not mated into which a user locates the first segment and the second segment of the suture such that the first segment and the second segment of the suture are fictionally secured along at least a portion of the capture zone when the mating portions are mated;
    wherein the first engaging element and the second engaging element, each part of a first clip and a second clip, respectively, that include a plurality of corresponding engaging elements, each connected to and separable from an adjacent engaging element along a longitudinal axis of the corresponding clip, each pair of corresponding first and second engaging elements mating with each other to constitute a separately deployable suture lock; and
    the connected engaging elements are in the form of a continuous series and are defined along the longitudinal axis of a strip of material by a series of indents oriented perpendicular to the longitudinal axis along the engaging element.

7. A method for securing sutures comprising:
providing at least one suture lock, the suture lock including a first engaging element and a second engaging element, each element including at least a mating portion which is opposed to and configured to mate with a corresponding mating portion of a surface of the other engaging element, the mating portions defining a non-through bore capture zone when not mated;
providing an applicator apparatus, the applicator apparatus including having a gripping end for holding the suture lock, the gripping end being operable between a substantially open orientation and a substantially closed orientation;
causing the suture lock to be operably positioned in the gripping end of the applicator apparatus, wherein the step of causing the suture lock to be positioned in the gripping end of the applicator apparatus comprises:
  loading at least a plurality of first engaging elements into the applicator; and
  causing the applicator to advance one of the first engaging elements into the gripping end,
  wherein the step of loading is performed by providing a first clip containing a continuous series of the first engaging elements and a second clip containing a continuous series of the second engaging elements, each clip being loaded into the applicator;
placing at least one suture segment across at least a portion of the non-through bore capture zone; and
operating the applicator apparatus to close the suture lock by causing mating of the first engaging element with the second engaging element such that the mating portions provide a frictional holding force along the non-through bore capture zone that secures the at least one suture segment in the suture lock.

8. The method of claim 7, wherein the method is performed endoscopically and the applicator apparatus includes a biasing element allowing a user to manipulate the applicator apparatus inside a patient's body from a location outside the patient's body.

9. The method of claim 7, wherein the step of placing the at least one suture segment across the non-through bore capture zone is performed by manipulating the applicator apparatus such that the at least one suture segment resides within the non-through bore capture zone in an orientation generally perpendicular to a longitudinal orientation of the suture lock.

* * * * *